(12) United States Patent
Volker et al.

(10) Patent No.: US 10,317,375 B2
(45) Date of Patent: Jun. 11, 2019

(54) METHOD AND APPARATUS FOR CHARACTERIZING A MEDIUM USING ULTRASOUND MEASUREMENTS

(71) Applicants: Nederlandse Organisatie voor toegepast-natuurwetenschappelijk onderzoek TNO, s-Gravenhage (NL); Sonaxis S.A., Besançon (FR)

(72) Inventors: Arno Willem Frederik Volker, s-Gravenhage (NL); Paul Louis Maria Joseph Van Neer, s-Gravenhage (NL); Guillaume Lucien Gérard Pierre, Besançon (FR); Francois Louis Denis Marie Bouvet, Besançon (FR); Sophie Crozat, Besançon (FR)

(73) Assignees: Nederlandse Organisatie voor toegepast-natuurwetenschappelijk onderzoek TNO, 's-Gravenhage (NL); Sonaxis S.A., Besancon (FR)

( * ) Notice: Subject to any disclaimer, the term of this patent is extended or adjusted under 35 U.S.C. 154(b) by 284 days.

(21) Appl. No.: 15/301,123

(22) PCT Filed: Mar. 31, 2015

(86) PCT No.: PCT/NL2015/050202
§ 371 (c)(1),
(2) Date: Sep. 30, 2016

(87) PCT Pub. No.: WO2015/152713
PCT Pub. Date: Oct. 8, 2015

(65) Prior Publication Data
US 2017/0023532 A1    Jan. 26, 2017

(30) Foreign Application Priority Data

Mar. 31, 2014 (EP) .................................... 14162671

(51) Int. Cl.
*G01N 29/52* (2006.01)
*G01N 29/46* (2006.01)
(Continued)

(52) U.S. Cl.
CPC ......... *G01N 29/52* (2013.01); *G01N 15/0255* (2013.01); *G01N 29/024* (2013.01);
(Continued)

(58) Field of Classification Search
CPC ...... G01N 29/52; G01N 29/46; G01N 29/343; G01N 29/032; G01N 29/024;
(Continued)

(56) References Cited

U.S. PATENT DOCUMENTS

2004/0139792 A1    7/2004    Cobb

OTHER PUBLICATIONS

Johan E. Carlson, Estimation of Particle Size Distributions in Solid/Liquid Suspensions Based on Wide-Band Ultrasound Attenuation Measurements, 2010 IEEE International Ultrasonics Symposium Proceedings, pp. 707-710.*

(Continued)

*Primary Examiner* — Toan M Le
(74) *Attorney, Agent, or Firm* — Banner & Witcoff, Ltd.

(57) ABSTRACT

Properties of a medium, such as its particle size distribution, are characterized using a measurement cell containing a medium between walls of the cell, with ultrasound transducers on opposite walls. Ultrasound is transmitted from the ultrasound transducers on both sides and transmission and reflection responses are detected. An ultrasound frequency dependent ratio of a Fourier transform value of a product of signals obtained from transmission responses in opposite directions and a Fourier transform value of a product of signals obtained from reflections at the transducers is computed. Preferably, the first received reflected and transmitted pulses in response to pulse excitation are used to compute (Continued)

the ratio. Ultrasound frequency dependent ultrasound speed and/or attenuation data of ultrasound in the medium are computed as a function of the ultrasound frequency from the ratio. This eliminates the effect of the walls.

18 Claims, 7 Drawing Sheets

(51) Int. Cl.
  *G01N 29/032* (2006.01)
  *G01N 29/024* (2006.01)
  *G01N 29/34* (2006.01)
  *G01N 29/44* (2006.01)
  *G01N 15/02* (2006.01)

(52) U.S. Cl.
  CPC ......... *G01N 29/032* (2013.01); *G01N 29/343* (2013.01); *G01N 29/4472* (2013.01); *G01N 29/46* (2013.01); *G01N 2291/02416* (2013.01); *G01N 2291/02818* (2013.01); *G01N 2291/044* (2013.01); *G01N 2291/048* (2013.01); *G01N 2291/102* (2013.01); *G01N 2291/105* (2013.01)

(58) Field of Classification Search
  CPC ....... G01N 2291/105; G01N 2291/048; G01N 2291/044; G01N 2291/02416; G01N 2291/012
  See application file for complete search history.

(56) References Cited

OTHER PUBLICATIONS

Carlson et al., A Simple Scattering Model for Measuring Particle Mass Fractions in Multiphase Flows, 2002, Ultrasonics 39, pp. 585-590.*

Hipp et al., Incorporating linear viscoelasticity into acoustic scattering theory, J. Acoustical Society of America, vol. 111, No. 4, pp. 1549-1551, Apr. 2002.

Hipp et al., Acoustic Characterization of Concentrated Suspensions and Emulsions. 1. Model Analysis, American Chemical Society, Langmuir, vol. 18, No. 2, pp. 391-404, 2002 (published on Web Dec. 12, 2001).

Hipp et al., Acoustic Characterization of Concentrated Suspensions and Emulsions. 2. Experimental Validation, American Chemical Society, Langmuir, vol. 18, No. 2, pp. 405-412, 2002 (published on Web Dec. 18, 2001).

Geers & Witt, Ultrasonic Extinction for In-line Measurement of Particle Size and Concentration of Suspensions and Emulsions, Sympatec GmbH, 2004.

Hartmann & Behrens, Simultaneous on-line analysis of solid concentration and particle size distribution of Gypsum Slurries applying Ultrasonic Extinction, ZKG International, vol. 59, No. 4, 2006.

Pankewitz & Geers, In-line Crystal Size Distribution analysis in industrial crystallization processes by Ultrasonic Extinction, LABO, No. 5, 2000.

Aug. 3, 2015—International Search Report and Written Opinion of PCT/NL2015/050202.

* cited by examiner

METHOD AND APPARATUS FOR CHARACTERIZING A MEDIUM USING ULTRASOUND MEASUREMENTS

CROSS-REFERENCE TO RELATED APPLICATIONS

This application is a U.S. National Stage application under 35 U.S.C. § 371 of International Application PCT/NL2015/050202 (published as WO 2015/152713 A1), filed Mar. 31, 2015, which claims the benefit of priority to EP 14162671.3, filed Mar. 31, 2014. Benefit of the filing date of each of these prior applications is hereby claimed. Each of these prior applications is hereby incorporated by reference in its entirety.

FIELD OF THE INVENTION

The invention relates to a method and an apparatus for ultrasound measurement, such as measurement of frequency dependent ultrasound speed and/or attenuation data. An embodiment relates to measurement of particle size distribution using ultrasound speed and/or attenuation data.

BACKGROUND

Ultrasound transmission spectroscopy uses measurements of the phase velocity (the sound speed) and attenuation as function of frequency to characterize a medium (e.g. a liquid). Applied to a medium containing suspended particles that affect ultrasound transmission through the medium, this may be used to determine statistical properties of the collection of particles, such as particle density, particle size distribution etc using inverse modelling.

Inverse modelling algorithms for determining particle size distribution from ultrasound speed and/or attenuation are known per se. Inverse modelling involves use of a model (also called the forward model) for predicting measured values as a function of values of parameters of the model. An inverse modelling algorithm uses actually measured values as input to estimate the values of the parameters that correspond to that input. Any model may be used, as long as it predicts ultrasound speed and/or attenuation with a reasonable accuracy given a particle size distribution. In a conventional model of ultrasound transmission by a medium with suspended particles, a low particle concentration approximation of the ultrasound frequency dependent ultrasound propagation speed $c(f)$ of a medium may be expressed as $$c(f)=c0+\text{integral of }N(d)*C1(f,d)$$

In the medium, the difference in ultrasound phase between points at distance z is $2*PI*z*f/c(f)$. Herein "c0" is a base value corresponding to the medium in the absence of particles. The second term represents the effect of the particles. The second term can be expressed as an integral over different particle sizes "d" of a product of the number of particles $N(d)$ of particles with a size "d" per unit volume (also called the volume fraction) times a function $C1(f, d)$ that expresses the change of ultrasound speed at the ultrasound frequency "f" due to a unit volume fraction of particles with size d.

The function $C1(f, d)$ may be determined in advance, for example by theoretical prediction, or by measuring ultrasound speed as a function of frequency when a known concentration at a concentration d is present in the medium. Function values for different f, d values may be provided stored in a look up table. In the case of high particle numbers, one or more additional terms corresponding to multiple scattering events, which are non-linear in N(d), may be added in the expression for c(f).

Similarly, the ultrasound frequency dependent ultrasound attenuation $a(f)$ of a medium may be expressed as $$a(f)=a0+\text{integral of }N(d)*A1(f,d)$$

Herein the function $A1(f, d)$ expresses the change of attenuation at the ultrasound frequency "f" due to a unit concentration of particles with size d. Like $C1(f,d)$, $A1(f,d)$ may be determined in advance. In the medium, the decrease in ultrasound amplitude between points at distance z is $\exp(-a(f)*z)$.

Conventionally, inverse modelling of the particle size distribution determines an estimate of $N(d)$ as a function of particle size "d" given measured ultrasound frequency dependent measurements of $c(f)$ and Usually, $N(d)$ itself is estimated as a parameterized function, for example as a normal distribution, or sum of normal distributions of which the mean, standard deviation and amplitude are estimated given the measurements of $c(f)$ and $a(f)$.

The basic set-up of such a transmission spectroscopy measurement comprises a measurement cell containing the medium and an ultrasound transmitter and receiver on opposite walls of the cell. Effects due to misalignment or differences in equipment behaviour can have a profound impact on the result when the frequency dependent variations in the sound speed due to the particles are quite small. This is especially important at low particle concentrations where there is less measurable variation in the sound speed. To measure very small particles, the upper frequency limit of the system needs to be increased—up to a few hundred MHz. At these frequencies the wavelength is very small, and therefore the demands for the system and electronics design strongly increase as well.

US2004139792 discloses use of ultrasound to determine component ratios and particle sizes of particles in a suspension. Ultrasound attenuation and phase delay of ultrasound transmission through the suspension are determined. The document notes that the attenuation coefficient of a material can be expressed as a logarithm of a ratio of the magnitude of received and transmitted signal spectra, divided by the distance over which attenuation takes place.

To protect the ultrasound transducers of US2004139792 they are separated by thick walls from the suspension. These walls give rise to reflections that may interfere with reception. To minimize these echoes US2004139792 tilts the transducers with respect to the centerline between them, and wedge shaped walls are used. Furthermore, a calibration procedure for a correction for the walls is disclosed. In the calibration procedure wall thickness is measured from the round trip time of ultrasound that reflects on the inner surface of the wall. Similarly, the attenuation coefficient for the walls is calculated from the attenuation of the round trip wave. Signals obtained after multiple reflections may be used for this.

SUMMARY

Among others, it is an object to provide for a method and apparatus for measuring ultrasound measurement wherein frequency dependence of the measurements that is unrelated to frequency dependence op propagation to the medium is reduced.

According to one aspect a method according to claim 1 is provided. Herein frequency dependent ultrasound speed and/or transmission data is obtained from a combination of ultrasound transmission measurements in opposite directions through a medium and adjacent walls of a measurement cell that contains a space for the medium and reflection measurements from opposite sides of the cell. A ratio of a Fourier transform value of a product of signals obtained from the first and second transmission response and a Fourier transform value of a product of signals obtained from the first and second reflection response is used to obtain frequency dependent ultrasound speed and/or attenuation data. In this way, frequency dependence due to effects of the walls can be substantially eliminated. This makes it possible to obtain estimates of the size distribution at lower concentrations and/or smaller particle sizes.

The Fourier transform values of the products of signals may be obtained by Fourier transforming the signals from the time domain and computing their products frequency by frequency. The ratio is a complex number. The frequency dependent ultrasound speed and/or attenuation data may be the amplitude and phase of the product respectively, or it may be obtained using the phase and amplitude. The natural logarithm of the amplitude equals the twice the attenuation coefficient times the distance between the walls and the phase equals twice this distance times the circular frequency divided by the ultrasound speed. As used herein both the attenuation coefficients and the attenuation during transmission between the walls will be referred to as attenuation. Similarly, both the speed and the inverse of the time delay during transmission between the walls will be referred to as speed. In another embodiment the data may be a complex phase factor of which the amplitude and phase represent the speed and attenuation or expressions containing these quantities.

In an embodiment, the transmission and reflection signals are detected by the second and first transducer in response to the same transmission by first transducer. Alternatively, time separated transmissions could be used, but use of the same transmission reduces dependence on time variation of ultrasound parameters and discrepancies between the transmitted signals. In addition, it may help to reduce dependence on time varying effects in the medium.

In an embodiment, the first and second wall and the first and second ultrasound transducer are arranged mirror symmetrically with respect to a virtual symmetry plane midway the first and second ultrasound transducer. This reduces the undesired frequency dependence. In a further embodiment the first and second wall have flat surfaces facing the interior space. This reduces the undesired frequency dependence.

In an embodiment an ultrasound pulse is transmitted from the first ultrasound transducer to the second ultrasound transducer and a second ultrasound pulse is transmitted from the second ultrasound transducer to the first ultrasound transducer, a processing system obtaining the signals obtained from the first and second reflection response by extracting earliest received response pulses the first and second reflection response. In this case, the Fourier transforms are each the Fourier transforms of a single extracted response pulse, excluding other received response pulses.

In this way the effect of frequency dependence due to effects of the walls can be substantially eliminated using a minimum of signal components. The earliest reflection, which occurs due to transmission through a wall, reflection from the interface between that wall and the medium and transmission back through the same wall, has a time delay with respect to the transmission that does not depend on the medium so that it can easily be extracted.

In a further embodiment the processing system obtains the signals from the first and second transmission response by extracting earliest received pulses the first and second transmitted response. In this way the effect of frequency dependence due to effects of the walls can be substantially eliminated using a minimum of signal components.

In an embodiment, the processing system computes an estimation of a particle size distribution of particles in the medium by applying an inverse modelling algorithm to the ultrasound frequency dependent ultrasound speed and attenuation data obtained from said ratio.

In an embodiment the inverse modelling algorithm uses input data that depends on a derivative with respect to ultrasound frequency of the ultrasound speed represented by said ratio and/or on a derivative with respect to ultrasound frequency of the ultrasound attenuation represented by said ratio. By using the derivative of the attenuation, the effect of the interfaces between the walls and the medium on the attenuation can be eliminated. By using the derivatives of the attenuation and the speed, effects of variability during particle growth can be eliminated.

In a further embodiment the inverse modelling algorithm uses a forward model that predicts the ultrasound frequency dependent ultrasound speed and attenuation dependent on the particle size distribution and a mass density of particles in the medium, the inverse modelling algorithm being used to obtain combined estimates of the particle size distribution and the mass density from the ultrasound frequency dependent ultrasound speed and attenuation data obtained from said ratio. It has been found that use of the mass density as an estimated parameter results in improved size distribution estimates.

In an embodiment, iteratively successive size ranges are used, respective particle size distributions being determined selectively for sizes in each size range using inverse modelling for the size range, widths and/or positions of successive ones of the size ranges each being selected based on the particle size distribution determined for a previous one of the size ranges, a size resolution in the size range being changed in correspondence with the selected width. In this way, high resolution can be obtained for narrow size distributions. In an embodiment, the width and/or position of the size range may be selected by excluding particle sizes at an edge of a previous size range for which less than a threshold density was determined using the previous size range. In an embodiment, the particle size distribution may be set to zero outside the size ranges.

In an embodiment the measurement may be performed while the particles grow in a vessel. The reduction of medium-unrelated frequency dependence makes it possible to monitor particle growth over a wider range of time. The measurement cell may be provided along a conduit in a probe bar that extends into the vessel. The conduit preferably runs from a first opening at an end surface of said bar to a second opening on a side surface of said bar. This ensures that flow of the medium through the cell does not stagnate. According to an aspect computer program product is provided that contains a computer program to make a programmable processing system perform the method. The computer program product may be a machine readable medium like a magnetic or optical disk or a (non-volatile) semi-conductor memory for example.

BRIEF DESCRIPTION OF THE DRAWING

These and other objects and advantageous aspects will become apparent from a description of exemplary embodiments by reference to the following figures.

DETAILED DESCRIPTION OF EXEMPLARY EMBODIMENTS

Figure 1:
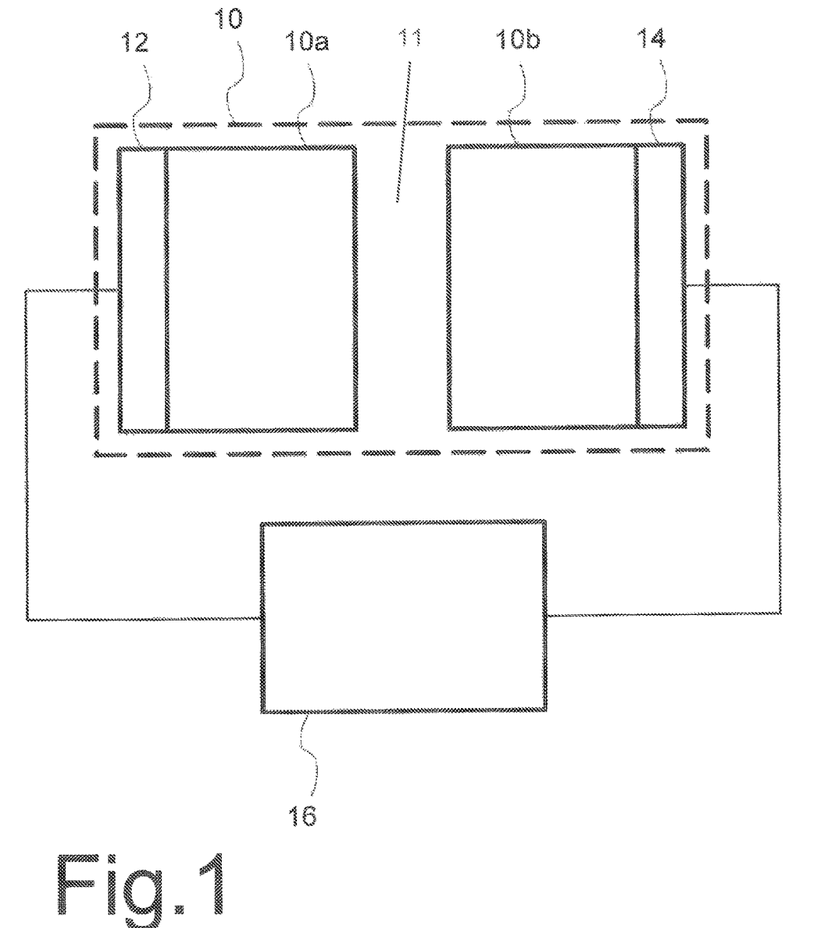
FIG. 1 schematically shows an ultrasound measurement apparatus.

FIG. 1 shows an ultrasound measurement apparatus. The apparatus comprises a measurement cell 10, a first ultrasound transducer 12, a second ultrasound transducer 14, and a processing system 16. Measurement cell 10 has walls 10a,b, defining an interior space 11 between walls 10a,b for a sample medium between the walls 10a,b. The walls may be of glass for example, with a thickness in a range of 1-10 millimeter for example, e.g. about 5 millimeters with a spacing between the walls of 1-10 millimeters for example, e.g. 3 mm. Walls 10a,b may in fact form part of a single wall that runs around interior space 11. As used herein, the parts of such a single wall on either side of interior space are referred to as walls. But interior space 11 need not be closed off in all directions by the walls In the figure measurement cell 10 is shown in a schematic cross-section through a first and second wall 10a,b, on opposite sides of the interior space 11 for the medium. First and second ultrasound transducer 12, 14 are provided on first and second wall 10a,b respectively, with first and second wall 10a,b between first and second ultrasound transducer 12, 14.

First and second ultrasound transducer 12, 14 are electronically coupled to processing system 16. The electronic coupling between first and second ultrasound transducer 12, 14 and processing system 16 may be configured to apply high frequency electrical signals to first and second ultrasound transducer 12, 14, which first and second ultrasound transducer 12, 14 convert into ultrasound, and to receive electrical signals that first and second ultrasound transducer 12, 14 produce by converting ultrasound into the electrical signals. The high frequency signal generator and receiver (or generators and/or receivers) for applying and receiving the electrical signals (not shown) may be considered to be part of processing system 16. Processing system 16 is configured to perform a computation to estimate a particle size distribution from signals measured using first and second ultrasound transducer 12, 14. Processing system 16 may comprise a programmable processor containing an instruction storage device with a program of instructions to make the processor perform said computation of the estimated particle size distribution.

In an embodiment, first and second ultrasound transducer 12, 14 and measurement cell 10 are configured to excite substantially plane waves in the medium. For this preferably use is made of purpose flat walls 10a,b and ultrasound transducers 12, 14 with radiating/receiving surfaces with a diameter many times larger than the ultrasound wavelengths used. The surfaces of walls 10a,b may be parallel to each other, as shown in FIG. 1. Alternatively, non planar structures may be used. For example, in another embodiment the surfaces of walls 10a,b that form the interface with the medium may be curved so as to act as an ultrasound lens that increases planarity of the ultrasound waves in the medium.

Preferably walls 10a.b and ultrasound transducers 12, 14 are mirror symmetric versions of each other with respect to a symmetry plane in interior space 11 midway between ultrasound transducers 12, 14.

Figure 2:
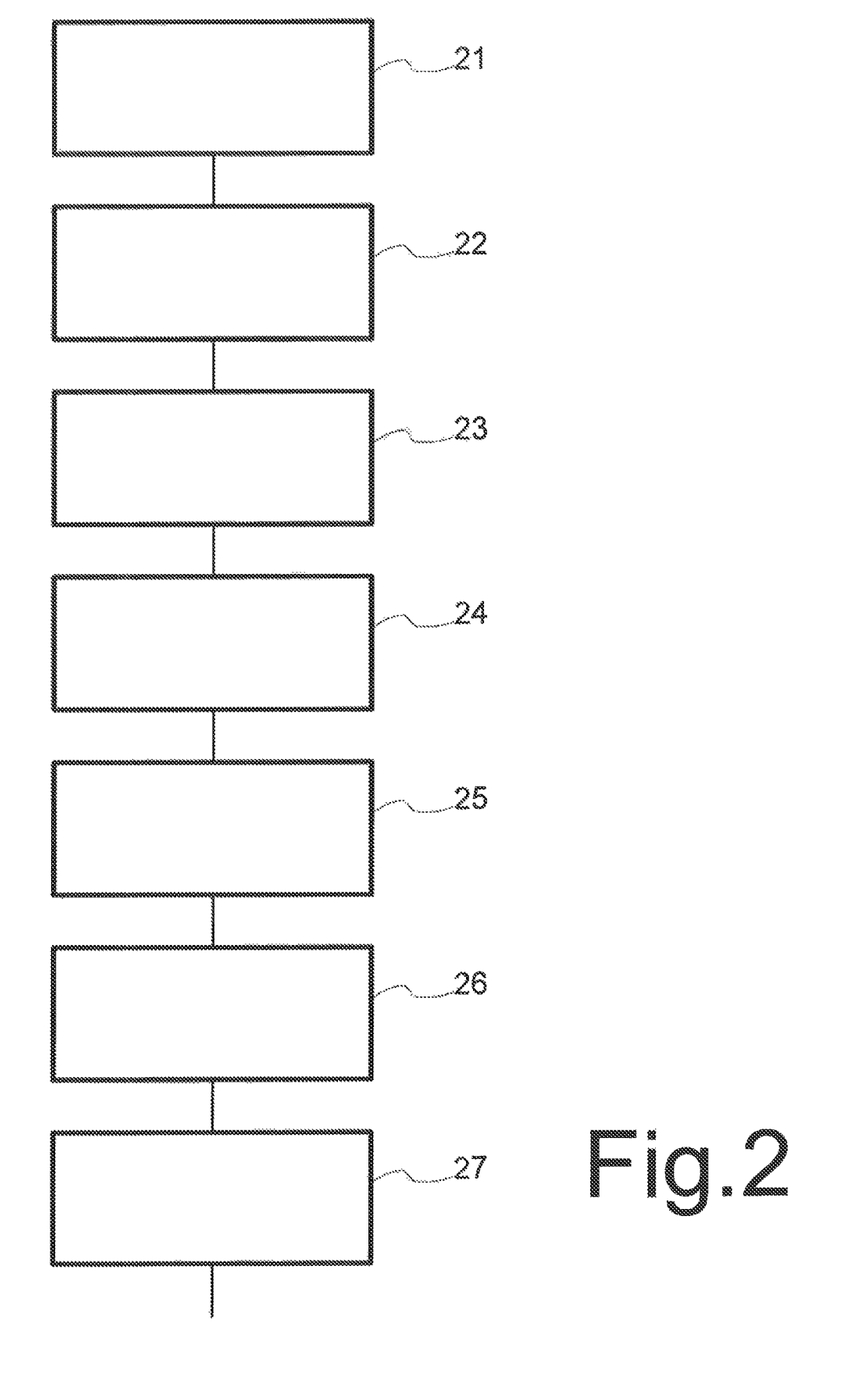
FIG. 2 shows a flow chart of a measurement process

Although an embodiment with a single transducers 12, 14 on each side has been shown it should be appreciated that instead arrays may be used. FIG. 2 shows a flow-chart of operation of the ultrasound measurement apparatus, performed when interior space 11 contains a medium comprising suspended particles. In a first step 21, processing system 16 causes first transducer 12 to transmit a first ultrasound pulse. In a second step 22, processing system 16 records responses to said first ultrasound pulse that are received by first and second ultrasound transducer 12, 14. In a third step 23, processing system 16 causes second transducer 14 to transmit a second ultrasound pulse. In a fourth step 24, processing system 16 records responses to said second ultrasound pulse that are received by first and second ultrasound transducer 12, 14, for example by storing digitized data representing samples of the detected response at successive sample time points in a memory of processing system 16. Band limited ultrasound pulses may be used, in which the ultrasound frequency range is not so small that overlap occurs between reflections of the pulses from the opposite walls. Although an embodiment has been described wherein the same pulse is used to produce the transmitted and reflected signals, it should be appreciated that alternatively time separated pulses may be used for transmission and reflection detection. Use of the same pulse has the advantage that the effect of time variations and/or discrepancies between pulses can be eliminated. Furthermore, instead of detections of transmitted and reflected signals from a single pulse an average of detections of transmitted and reflected signals from a plurality of pulses may be used. The recorded transmission signals can be used to determine ultrasound propagation speed and attenuation in the medium, including particles suspended in the medium, because the signals depend on the transmission coefficient of the medium. The presence of suspended particles introduces a frequency dependence into the propagation speed and attenuation in the medium. However, the recorded transmission signals also depend on ultrasound transmission coefficients of the walls 10a,b on either side of the medium and ultrasound transmission coefficients of the interfaces between the walls and the media or vice versa.

The recorded reflection signals also depend on ultrasound transmission coefficients of at least one of the walls 10a,b. Furthermore they depend on ultrasound reflection coefficients of the interfaces between the walls and the medium. When ultrasound pulses from first and second ultrasound transducer 12, 14 are used, the earliest arriving reflected pulse involves transmission in mutually opposite directions through the wall 10a,b on which the ultrasound transducer 12, 14 is located, and reflection from the interface of that wall with the medium. The earliest arriving transmitted pulse after transmission from first ultrasound transducer 12 involves transmission in a first direction through the medium, both walls 10a,b and both interfaces of the medium with the walls 10a,b. The earliest arriving transmitted pulse after transmission from second ultrasound transducer 14 the same transmission, but in a second direction opposite to the first direction.

In a fifth step 25, processing system 16 uses the recorded reflection signals to extract the components due to reflection from the interface between the medium and the wall 10a,b on which the transmitting transducer 12, 14 is located. When the transmitted signals are pulses, these components may be selected by time windowing, to select only a single reflected pulse. In the reflected signal the extracted component is the earliest reflected pulse. Later arriving reflected pulses, which correspond to reflection from the interface with the opposite wall and possibly from multiple reflections, are blocked. The extracted pulses can easily be selected, because the time delay between their reception and transmission is due to the wall only, and exhibits little or no dispersion or variability.

Optionally, processing system 16 may apply a similar extraction of the first arriving pulse from the recorded transmission signals. This may be used to suppress later arriving transmitted pulses due to multiple reflections.

In a sixth step 26, processing system 16 computes a ratio $T1(f)*T2(f)/(R1(f)*R2(f))$ of a first product $T1(f)*T2(f)$ and second product $R1(f)*R2(f)$. The first product is the frequency-by-frequency product of Fourier transforms $T1(f)$ and $T2(f)$ of the detected transmitted signals of the first and second ultrasound transducers 12, 14, optionally obtained after extracting a single pulse from the received signal, e.g. the earliest arriving pulse. The second product is the product of the earliest detected reflection signals $R1(f)$ and $R2(f)$ of the first and second ultrasound transducers 12, 14, obtained after extracting after extracting a single pulse from the received signal, e.g. the earliest arriving pulse. The resulting ratio $T1(f)*T2(f)/(R1(f)*R2(f))$ is a complex factor, which depends on ultrasound frequency at least due to the presence of particles in the medium that affect transmission through the medium in a frequency dependent way. The range of Fourier transform frequencies may be limited to ultrasound frequencies at which ultrasound wavelength in walls $10a,b$ is no more than half an preferably less than a tenth of the transmission/reception opening of ultrasound transducers 12, 14.

Although an example has been described wherein values of the Fourier transform of the product are computed by computing the Fourier transforms before computing frequency-by-frequency products, it will be appreciated that instead convolutions could be computed in the time domain, the values of the Fourier transform of the product being computed by computing a Fourier transform of the convolution.

In the computed ratio $T1(f)*T2(f)/(R1(f)*R2(f))$, the contributions due to transmission factors corresponding to transmission through the walls drop out, because they occur in the same way in both products $T1(f)*T2(f)$ and $R1(f)*R2(f)$. The transmission signals $T1(f)$ and $T2(f)$ each result from transmission through the medium and both walls and the reflection signals $R1(f)$ and $R2(f)$ each result from transmission back and forth through a respective one of these walls. As a result, the ratio only depends on the square of the transmission factor M of the medium and a ratio of transmission and reflection factors of the interfaces. The latter ratio is generally frequency independent and real-valued, effectively with zero phase. Therefore, the phase PHI of the overall ratio corresponds to twice the phase shift due to the medium in interior space 11, including the effect of particles in the medium. From this phase PHI, the speed of sound c in the medium can be determined according to $c=PI*L*f/PHI$, wherein L is the distance between the interfaces on opposite sides of interior space 11 and f is the frequency of the spectral component for which the phase PHI is determined.

The derivative with respect to frequency of the absolute value of the ratio between the products equals the derivative of the square of the ultrasound attenuation factor by the medium.

As will be appreciated part of the effects of the walls drop out exactly from the ratio because the forward wave propagation from each ultrasound transducer 12, 14 through the wall $10a, b$ on which it is located is the same for both transmission and reflection. The effect of backward transmission through that wall as part of reflection and forward transmission of waves due to transmission from the opposite ultrasound transducer cancel approximately. Differences between the wave front reflected by the interface of the wall and the medium and the wave front of ultrasound that is transmitted by the interface from the opposite transducer can lead to imperfect cancellation. When there is perfect plane transmission, they cancel exactly. Therefore, the parallel orientation of the surfaces of the walls shown in FIG. 1 improves this cancellation. When the wall surfaces are flat as shown in FIG. 1, the cancellation improves due to decreased wave divergence. With decreasing distance between the flat interfaces of the opposite walls with the medium, the differences between the reflected wave front and the transmitted from the opposite side decreases.

Preferably, electronic switches are provided between the high frequency signal generator(s) from the first and second ultrasound transducer. The electronic switches may be used to isolate the high frequency signal generator(s) from the first and second ultrasound transducer during the measurement of both the transmitted and the reflected signals. The switches are used to connect the high frequency signal generator(s) to the ultrasound transducer when the transducers transmit the ultrasound by conversion of the electrical signal from the generator(s) to ultrasound. By isolating the generator(s) from the transducers during measurement, the effect of the generator(s) on differences between measurements of the reflected wave front and the transmitted wave front may be reduced.

In an embodiment, the computed ratio may comprise a ratio of the products multiplied by a correction factor that compensates for the imperfect cancellation. The correction factor is substantially independent variation of properties of the medium (optionally it may be selected dependent on the properties of the medium in the measuring range). The value of the correction factor may be determined by a test measurement.

In an embodiment, the product of Fourier transforms of the earliest reflected pulse may be replaced by a square root of a product of Fourier transforms of the earliest pulse in the reflected signal and the next pulse in that signal (the latter being due to reflection off the opposite interface). In this way effects of divergence may be averaged out. Instead of using the square root, a ratio with a square of the product of the transmitted signals may be used. Alternatively, the imperfections of cancellation can be reduced to an acceptable level by reducing the distance. Alternatively, the walls may be shaped so that flat wave fronts are produced in the interior space.

In a seventh step 27, processing system 16 executes an inverse modelling algorithm, to estimate parameters of the particle size distribution from the ratio of the products as a function of ultrasound frequency, or at least the phase and/or absolute value of that ratio.

Inverse modelling of a particle size distribution is known per se. Inverse modelling uses a forward model that describes wave propagation in suspensions. Inversion is the determination of the parameters of the model (e.g. parameters that define concentration as a function of particle size from the measured sound speed and attenuation. Based on a measured sound speed and attenuation the most likely concentration at a selected particle sizes may be determined for example. On way of performing inverse modelling comprises use of a nonlinear least squares methodology. Here the (length of the) following error vector ($\varepsilon_K$) is minimized:

$$\left(\frac{K(f_1)}{k_1(f_1)}\right)^2 - \left(\frac{K_s(f_1)}{k_1(f_1)}\right)^2 @:@\left(\frac{K(f_m)}{k_1(f_1)}\right)^2, \quad (1)$$

The @ sign is used to indicate other components of the error vector $\varepsilon_K$ for successive measured frequencies $f_1 \ldots f_m$. m is the number of measured frequencies. K is the effective wave number, which contains the speed of sound (c) and the attenuation according to $K=\overline{\omega}+i\alpha$ (omega is two pi times f and alpha is the attenuation coefficient) and k is the wave number in the absence of particles. The subscript e stands for the estimated values. Instead deviations between one and ratios between the measured and estimates K values may be used as error vector components.

The estimated terms in the equation for the error vector follow from a forward model. The forward model for sound propagation may be written as:

$$\frac{K(f)^2}{k_1(f)^2} = 1 - \sum_{r=r_{min}}^{r_{max}} L(f \cdot r)\phi(r) - \sum_{r=r_{min}}^{r_{max}} Q(f \cdot r)\phi(r)^2 \quad (2)$$

$$L(f, r) = \frac{3i}{k_1^a r^3} \sum_{n=0}^{\infty} (2n+1)A_n \quad (6)$$

$$Q(f, r) = \frac{9}{4k_1^6 r^6}[\text{sum of product terms of } A_n] \quad (3)$$

Herein r is the particle size and phi(r) is the number of particles at the size r. L(f,r) are primary scattering coefficients and Q are coefficients of multiple scattering. When discrete grid of size values r and discrete frequency values are used, L and Q are matrices. To minimize discretization errors in the calculation of L and Q it is recommended to use a fine grid for r.

The matrices L, Q can be calculated a-priori based on a model. A known model is the ECAH-model, after the developers (Epstein, Carhart, Allegra, Hawley). The model describes the interaction of a sound wave in an infinite medium with particles. The incident wave field is expressed as an infinite summation over Bessel functions, Hankel functions, Legendre and associated Legendre polynomials. Boundary conditions are applied to the liquid particle interface. This yields a number of coefficients. These coefficients are the so called scattering coefficients: $A_n$, $B_n$, $C_n$, $A'_n$, $B'_n$, $C'_n$, here n is the order of the scattering coefficient, $A_n$ is the coefficient of the scattered pressure wave field in the medium, $B_n$ is the coefficient van de thermal wave in het medium, $C_n$ is the coefficient of the shear wave in the suspending medium. The coefficients with a prime, are the same physical quantity but inside the particle. The scattering coefficients are calculated by solving the following set of linear equations:

$$v_n + M_n \begin{bmatrix} A_n \\ B_n \\ C_n \\ A'_n \\ B'_n \\ C'_n \end{bmatrix} = 0, \quad (4)$$

Where the vector $v_n$ and the matrix $M_n$ contain various physical constants, Bessel functions and Hankel functions. These equations are derived from boundary conditions at the interface. For more detail, the reader is referred to articles by Allegra and Epstein.

The ECAH model is a single scattering model. The total effect of a large number of particles is obtained by summation over the contribution of all particles. This yields to an expression of the attenuation in the medium:

$$\alpha = -\frac{3\phi}{2k_1^2 r^3} \sum_{n=0}^{\infty} (2n+1)\text{Re}(A_n), \quad (5)$$

Where $\alpha$ is the attenuation, $k_1$ is the wave number of the incident pressure wave, r is the radius of the particle, $\phi$ is the volume fraction. Depending on the particle size compared to the wavelength, these series is truncated. Extension to multiple scattering is possible, this means that the incident wave field consists of the primary wave and scattering contributions of other particles. A number of different models exist that include this effect. The equation below is derived by Fikioris en Waterman containing only the $A_0$ en $A_1$ coefficients:

$$\frac{K^2}{k_1^2} = 1 - \frac{3i\phi}{k_1^3 r^3}(A_0 + 3A_1) - \frac{27\phi^2}{k_1^6 r^6}(A_0 A_1 + 2A_1^2), \quad (6)$$

where K is the effective wave number, from which the speed of sound (c) and the attenuation can be calculated according to $K=\overline{\omega}/c+i\alpha$, where $\overline{\omega}$ is the angular frequency.

Alternatively Lloyd and Berry derived a more generic alternative form that also includes multiple scattering:

$$\frac{K^2}{k_1^2} = 1 - \frac{3i\phi}{k_1^3 r^3} \sum_{n=0}^{\infty} (2n+1)A_n - \quad (7)$$

$$\frac{9\phi^2}{4k_1^6 r^6}\Big[12A_0 A_1 + 40A_0 A_2 + 84A_0 A_3 + 144A_0 A_4 + 24A_1^2 +$$

$$132A_1 A_2 + 264A_1 A_3 + 444A_1 A_4 + \frac{920}{7}A_2^2 + \frac{1444}{3}A_2 A_3 +$$

$$\frac{60120}{77}A_2 A_4 + \frac{12656}{33}A_3^2 + \frac{169020}{143}A_3 A_4 + \frac{842256}{1001}A_4^2 + \ldots \Big]$$

In an embodiment the range ultrasound frequencies for which measurements are used in the inverse modelling is limited to ultrasound frequencies at which ultrasound wavelength in walls 10a, b is no more than half an preferably less than a tenth of the transmission/reception opening of ultrasound transducers 12, 14. This reduces frequency dependent effects due to non-planar transmission.

When band limited pulses are used, the pulse bandwidth preferably extends over the entire range of frequencies that is used in the inverse modelling algorithm. Alternatively, a plurality of pulses with narrower bands at different frequency positions may be used to compute ratios in the different frequency bands. In this case the ratios from pulses in a combination of different bands may be used as input for inverse modelling.

It should be appreciated that the dependence on transmission through the walls can also be eliminated using other embodiments than that if FIG. 2. This embodiment uses a ratio of transmissions measured from first arriving pulses between the transducers and reflection measured from the earliest reflected pulses at the transducers on both sides (the reflections from the closest interfaces to the medium). In alternative embodiments later arriving reflections and/or transmissions may be used. However, the use of earliest reflections makes it easier to identify the relevant pulses robustly, and the use of transmission and reflection from both sides makes this possible.

In general, later reflections involve added even numbers of transmissions through one or more of the medium and the walls, and an added even overall number of reflections from the surfaces of the walls. Any ratio could be used of a numerator and a denominator that involve the same number of the transmissions through the walls, but different numbers of transmissions through the medium. For example use may be made of the ratio of (a) the product of reflection measured from the next after earliest arriving reflected pulses (corresponding to transmission through one wall, the medium and back), and (b) a product of transmissions measured from the first arriving transmitted pulse.

As another example, use may be made of the ratio of (c) a product of transmissions measured from the next after earliest arriving transmitted pulse and (d) the product of reflection measured from the earliest or next after earliest arriving reflected pulses. Use of a ratio that is invariant for interchange of the roles of the transducers reduces errors due to asymmetry of the cell.

In another example use could be made of the ratio of (e) reflection measured from the earliest second arriving reflected pulse at a first transducer and (f) reflection measured from next after earliest the second arriving reflected pulse at the same first transducer. In general, any pulse from one transducer arriving at the other transducer is a result of travel for an odd number of times through the medium and through each of the walls (not necessarily the same number of times: multiple reflections at the interfaces may add an even number of transmissions through the media, but not through the walls). Similarly, any pulse from one transducer reflected to that transducer is a result of travel for an even number of times (in some cases zero times) through the medium and through each of the walls. From these numerators and a denominator that involve the same number of the transmissions through the walls but different numbers of transmissions through the medium.

As noted, some of these examples may make it more difficult to avoid errors due to confusion between received pulses. Also the use of an increasing number of reflections and/or transmissions through the interfaces and extended path length reduce accuracy.

Although examples using pulses have been described, it should be realized that alternatively other types of transmitted signals can be used, such as continuous waves with swept frequency or a series of continuous waves with different frequencies. From the responses to such signals pulse responses may be synthesized.

Figure 3:
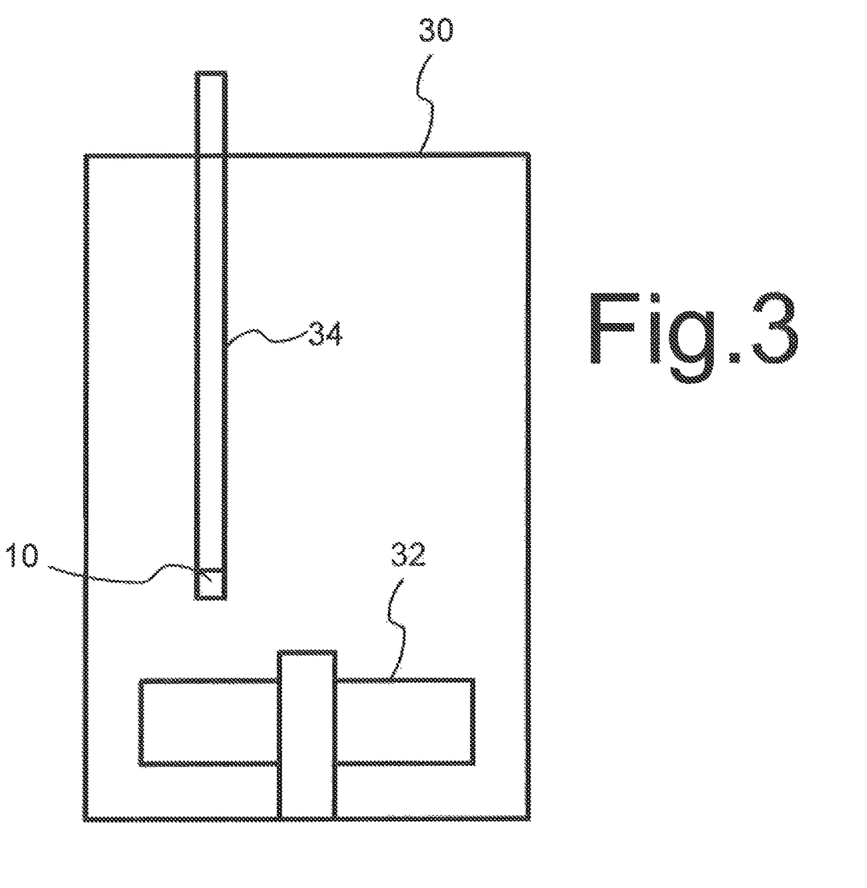
FIG. 3, 3a, 3b shows a particle forming apparatus
Figures 3A, 3B:
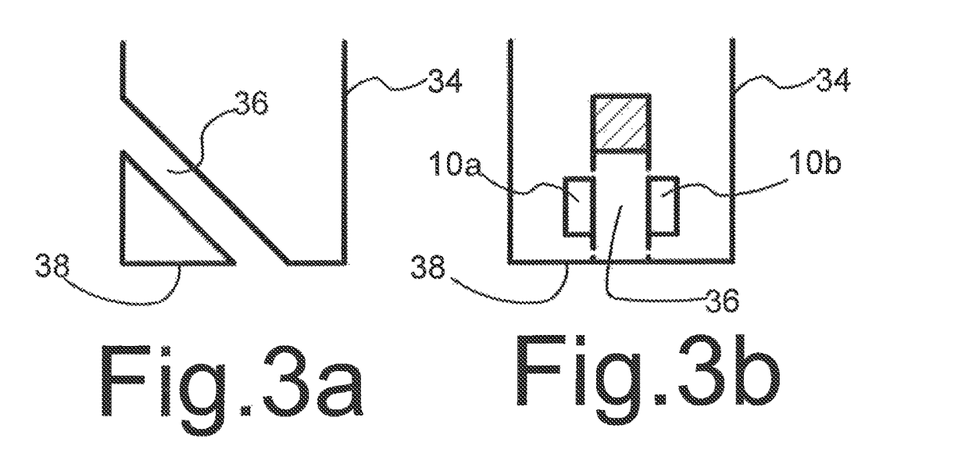

FIG. 3 shows an exemplary apparatus for particle forming, comprising a vessel 30, an impeller 32 in vessel 30 and the ultrasound measuring apparatus. the ultrasound measuring apparatus comprises a sensing bar 34 that extends into vessel 30, and the measuring cell 10 near the tip of the sensing bar. FIGS. 3a and 3b show the tip of sensing bar 34 in more detail from two orthogonal directions. A channel 36 is provided in sensing bar 34, and walls 10a,b of measuring cell 10 from part of the walls of channel 36. Channel 36 runs from a first opening on the side of sensing bar 34 to a second opening on the tip 38 of sensing bar 34. The first and second opening in the surface of sensing bar 34 at the ends of channel 36 are provided to allow liquid from vessel 30 to pass through channel 36 between the openings. As a result of liquid flow the liquid will flow between walls 10a,b. In operation, vessel 30 may contain a liquid medium such as water with dissolved SiO2, from which SiO2 nano-particles are formed by crystallization in vessel 30 (e.g. particles with diameters in the range of 10 to 200 nanometer). Impeller 32 causes the liquid to circulate in vessel 30 during particle forming by crystallization.

The ultrasound measurement apparatus is used to monitor the formation of particles by determining an estimated size distribution of the nano-particles during the particle forming process. However, it should be appreciated that the ultrasound measurement apparatus may alternatively be used to estimate size distribution of other particles during crystallization or of nano-particles or other particles apart from crystallization.

The liquid flow through vessel 30 caused by impeller 32 is associated with pressure differences in vessel 30, including a difference between the pressure at the first and second opening in sensing bar 34. This pressure difference causes liquid flow through channel 36. In the illustrated embodiment, sensing bar 34 is located at a position in vessel 30 where the liquid flow along sensing bar 34 has a direction component towards the tip 38 of sensing bar 34. Tip 38 may be located at a position where rotation of impeller 32 draws liquid from the surrounding of tip 38 away from sensing bar 34. As a result the second opening at the end of channel 36 on tip 28 lies in the wake of sensing bar 34, so that the pressure at the second opening will consistently be lower that that at the first opening on the side of sensing bar 34. This ensures consistent flow of liquid with crystallizing particles through the measuring cell 10.

Instead of a sensing bar another support structure may be used with a channel and first and second openings, with part of a wall of the channel being formed by the walls of the measuring cell. Preferably, the channel runs from a first opening on a side surface of said support structure to a second opening in an end surface of said support structure, the end surface at the second opening forming a non-zero angle with the side surface at the first opening. This enables positioning of the second opening in the wake, with the other upstream. Preferably, the side surface goes over into the end at a localized an angle (e.g. a perpendicular angle as shown in the figures). This helps to ensure lower pressure at the second opening.

Alternatively, the first and second openings may be located on opposite sides of a support structure like sensing bar 34. This may also provide for flow through channel 36. But makes the angle at which sensing bar 34 is placed in vessel 30 more critical to obtain measurement of the size distribution that track developments in vessel 30. This critical dependence can be reduced by providing the second opening in sheltered part of the side, e.g. a part where the surface deviates at an angle inward from the remainder of the side. However, because of the wide range of viscosity values that can arise in nano particle growth processes, with a corresponding variation of the hydrodynamic boundary layer thickness, it is difficult to design surfaces on the side of the sensing bar that work well over the whole range of viscosity values. Use of the tip 38 for the second opening simplifies this.

In other alternatives, the measuring cell 10 may be located elsewhere in vessel 30, for example in or on the drive shaft of impeller 32, or on the wall of vessel 30. Other types of stirring element may be used instead of, or in addition to, impeller 32, such as paddles that are moved through vessel 30. Independent of the use of the ratios, an ultrasound measuring apparatus is provided, comprising a first ultrasound transducer and a second ultrasound transducer;
a measurement cell having a first and second wall defining an interior space between the first and second wall, the first and second ultrasound transducer being located on the first and second wall respectively, with the walls and the interior space between the transducers;
a support structure with a channel through said support structure, part of a wall of the channel being formed by the walls of the measuring cell, the channel running from a first opening on a side surface of said support structure to a second opening in an end surface of said support structure, the end surface at the second opening forming a non-zero angle with the side surface at the first opening. In a further embodiment of this apparatus the support structure is a sensing bar, the first opening being located on a side surface the sensing bar and the second opening being located in a tip surface of the sensing bar.

It has been found that, for nano-particles and also for other particles formed by crystallization, imperfections during growth (especially early growth) can affect the reliability of the size distribution estimation by means of the ultrasound measurement apparatus. Especially for small particles the effects of imperfections may be significant compared to the overall effect of the particle.

It has been found that most, but not all, of the effects of the imperfections on the size distribution estimation by means of ultrasound measurement can be avoided by applying inverse modelling using a model for the frequency derivates of the ultrasound propagation speed and attenuation. The only effects of the imperfections that cannot be substantially eliminated in this way is the effect of mass density, that is, variability of the weight to volume ratio of the particles e.g. due to crystal vacancies. The particle weight per unit medium volume can be significant e.g. 2200 kg/cubic meter compared to 1000 kg/cubic meter for water without particles.

Figure 4:
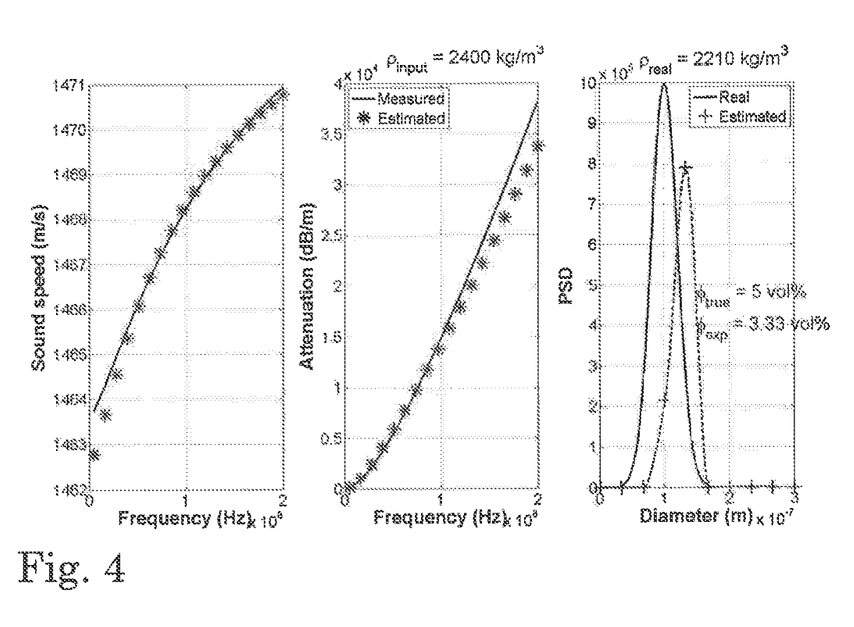
FIG. 4 shows graphs responses and particle size distribution

FIG. 4 (solid line rightmost graph) shows a graph of an exemplary particle size distribution and simulated corresponding sound speed and attenuation for a mass density of 2210 kg per cubic meter (solid line left and middle graph). The dashed line in the rightmost graph and the stars in the left and middle graph show the results of inverse modelling using a different mass density of 2400 kg per cubic meter. As can be seen, this results in a significantly wrong inverse modelled particle size distribution.

It has been found that in practice the disturbing effect of the imperfections that affect mass density can be substantially suppressed by including overall particle mass density rho in terms of particle weight per unit medium volume as an estimated parameter in the model used in the inverse modelling process. The particle mass density may be represented indirectly by the overall mass density of the medium including the particles (particle weight per unit medium volume or overall weight per unit medium volume) That is, instead of functions $C1(f,d)$ and $A1(f,d)$, functions $C1(f,d,\text{rho})$ and $A1(f, d, \text{rho})$ are used in the model, wherein $C1(f,d,\text{rho})$ and $A1(f, d, \text{rho})$ may be predetermined functions provided for example by means of a stored look up table in processing system 16.

Independent of the use of the ratios, a method of ultrasound reflection measurement is provided that uses a measurement cell containing a medium and a first ultrasound transducer and a second ultrasound transducer on mutually opposite first and second walls of the cell respectively, the method comprising transmitting ultrasound from the first ultrasound transducer to the second ultrasound transducer, through the walls of the measurement cell and the medium between the walls;
using the second and first ultrasound transducer to detect a transmission response and/or a reflection response to the ultrasound using transmitted by the first ultrasound transducer;
computing ultrasound frequency dependent ultrasound speed and/or attenuation data of ultrasound in the medium a function of the ultrasound frequency from at least the transmission response and/or the reflection response;
estimating a particle size distribution of particles in the medium by using a processing system to apply an inverse modelling algorithm to the ultrasound frequency dependent transmission response and/or reflection response, using a forward model that predicts the derivatives of ultrasound frequency dependent ultrasound speed and attenuation dependent on the particle size distribution and a mass density of particles in the medium, the inverse modelling algorithm being used to compute combined estimates of the particle size distribution and the mass density from the ultrasound frequency dependent ultrasound speed and/or attenuation data.

A computer programming product, comprising a program of instructions for a programmable processing system is provided that, when executed by the programmable processing system, will cause the programmable processing system to perform this method.

Similarly, an ultrasound measuring apparatus is provided, comprising a first ultrasound transducer and a second ultrasound transducer;
a measurement cell having a first and second wall defining an interior space between the first and second wall, the first and second ultrasound transducer being located on the first and second wall respectively, with the walls and the interior space between the transducers;
a processing system configured to
receive a detected transmission response received by the second transducer in response to ultrasound transmitted by the first ultrasound transducer and/or receive a detected reflection response received by the first ultrasound transducer in response to ultrasound transmitted by the first ultrasound transducer
compute ultrasound frequency dependent ultrasound speed and/or attenuation data of ultrasound in the medium a function of the ultrasound frequency from at least the transmission response and/or the reflection response;
estimate a particle size distribution of particles in the medium by applying an inverse modelling algorithm to the ultrasound frequency dependent ultrasound speed and/or attenuation data, wherein the processing system is configured to use a forward model in said inverse modelling algorithm that predicts the ultrasound frequency dependent ultrasound speed and attenuation dependent on the particle size distribution and a mass density of particles in the medium, the processing system being configured to use the inverse modelling algorithm to obtain combined estimates of the particle size distribution and the mass density from the ultrasound frequency dependent ultrasound speed and/or attenuation data.

Figure 5:
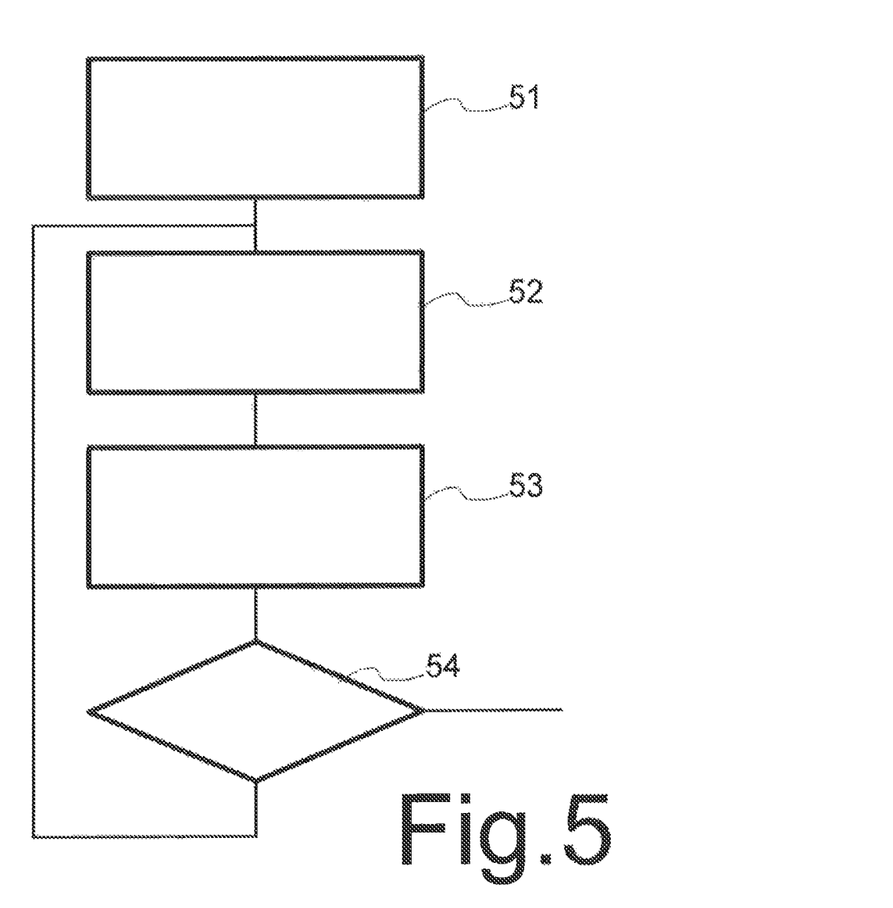
FIG. 5 shows a flow chart of an improved inverse modelling process
Figure 6:
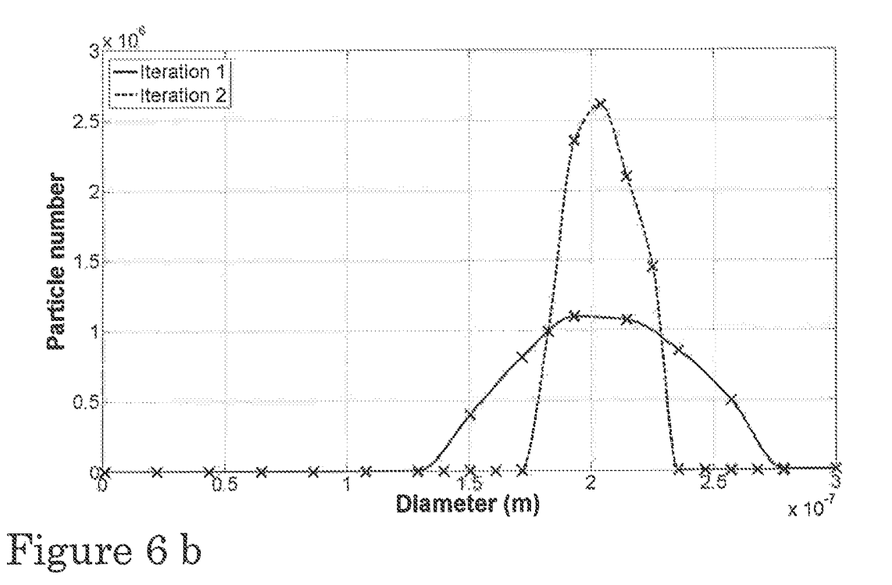
FIG. 6 shows iterated size distributions with increasing resolution
Figure 6A:
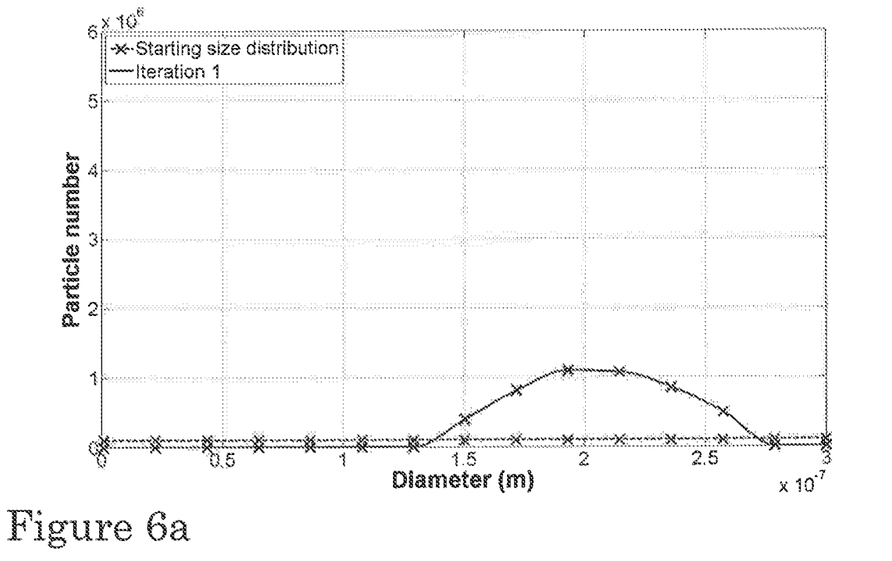
Figure 6C:
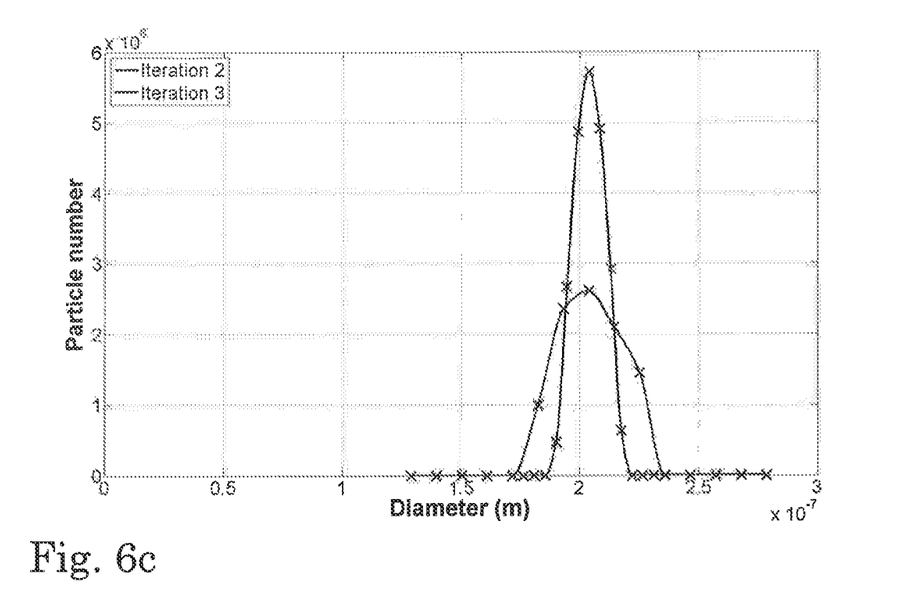
Figure 6D:
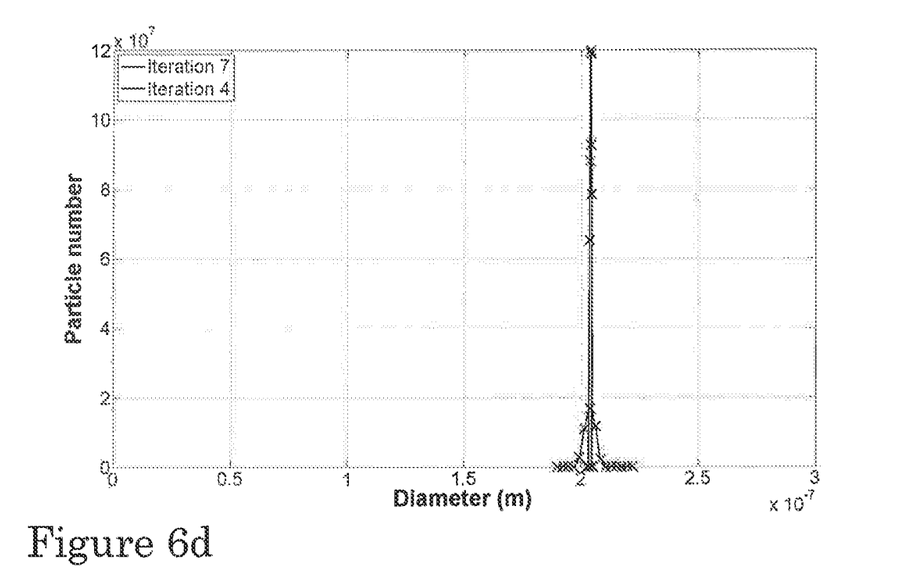

FIG. 5 shows a flow-chart of a special inverse modelling algorithm wherein adjustable focus ranges are used for the particle size. The special inverse modelling algorithm uses measured ultrasound propagation speed and attenuation as input. In the model an adaptable parameterization of the particle size distribution is used. The model used for inverse modelling provides for selection of an adaptable range of particle sizes d where the number of particles N(d) is allowed to be non-zero, the location of that range being adaptable. More generally, the model may allow for different size resolution of the distribution N(d) in different ranges of particle sizes d, the location of the size range with maximum resolution being adaptable.

In an embodiment, the distribution N(d) may be expressed as an interpolation from sample values N(d(i)) of the distribution at a set of particle sizes d(i) (i being an index), only the values N(d(i)) in the adaptable range being allowed to be non-zero. More generally N(d) may be modelled as a sum of terms w(i)*Fi(d−d(i)), wherein w(i) are the parameters and Fi are predetermined functions, the functions Fi used for sizes d(i) in the adaptable range decreasing more sharply with increasing absolute value of d−d(i) than the functions used outside it. Correspondingly, the particle sizes d(i) may lie more densely in a adaptable range of particle sizes than outside that range. This is important for measuring the particle size distribution of nano particles during growth, because the shape of the particle size distribution during such a growth process is complex, and there is a need to detect complex deviations.

In a first step 51, processing system 16 makes an initial selection of said adaptable range. A range may be selected that covers all possible particle sizes where significant density can be expected. In a second step 52, processing system 16 executes a conventional inverse modelling algorithm, wherein the selected range is kept fixed. In a third step 53, processing system 16 determines an iteratively next range wherein at least a predetermined fraction of the estimated size distribution from second step 52 is concentrated. In a fourth step 54, processing system 16 tests whether the iteratively next range differs by less than a predetermined amount from the range used in second step 52. If so processing system 16 stops the process. If not, processing system 16 repeats from second step 52 using the iteratively next range as said of said adaptable range.

In an embodiment, processing system 16 is configured to narrow the iteratively next range in successive executions of third step 53, each time selecting a central position of the narrowed range dependent on the estimated size distribution from the preceding second step 52. The width of the range may be determined based on the distance from the central position beyond which the estimated size distribution from the preceding second step 52 remains below a threshold. In a further embodiment, processing system 16 may be configured to select increases as well as decreases of the range.

Processing system 16 may be configured to increase the width for example if the estimated size distribution from the preceding second step 52 is not below a threshold at an edge of the range. In this embodiment fourth step 54 may involve a test whether the iterations have started alternatively increasing and decreasing the size of the range. Alternatively, processing system 16 may be configured to allow shifts of the range without narrowing as well, for example when the previously estimated size distribution remains significant at one edge of the adaptable range used in second step 52.

FIG. 6a-d compares estimations of the particle size distribution estimated by means of the process of FIG. 5 after the first, second, third and seventh iterations with previous iteration, for a simulated "true" size distribution that is a narrow peak at 20 micrometer with a standard deviation of two nanometers and integrated peak height of 10 volume percent. In each figure the sharpest curve corresponds to the higher number of iterations. Of course in practice the true size distribution will not be so simple, but this distribution is used to illustrate that a model using sample values for selected particle sizes, which enables handling complex size distributions, can be made to handle such sharp distributions.

The successively selected adaptable ranges are shown by means of crosses indicating particle sizes d(i) at which sample values N are modelled. As may be seen, the process allows for improved resolution of a narrowly distributed particle size distribution. Such narrow distributions typically occur during nano-particle growth. Application of an inverse modelling algorithm with an adaptable focus range to nano-particle growth monitoring provides for more accurate estimation of the particle size distribution. As can be seen the iterations converge towards the narrow peak of the simulated true distribution.

Independent of the use of ratios, a method of ultrasound reflection measurement is provided that uses a measurement cell containing a medium and a first ultrasound transducer and a second ultrasound transducer on mutually opposite first and second walls of the cell respectively, the method comprising transmitting ultrasound from the first ultrasound transducer to the second ultrasound transducer, through the walls of the measurement cell and the medium between the walls;

using the second and first ultrasound transducer to detect a transmission response and/or reflection response to the ultrasound using transmitted by the first ultrasound transducer;

computing ultrasound frequency dependent ultrasound speed and/or attenuation data of ultrasound in the medium a function of the ultrasound frequency from the transmission response and/or the reflection response;

estimating a particle size distribution of particles in the medium by using a processing system to apply an inverse modelling algorithm to the ultrasound frequency dependent transmission response, for iteratively successive size ranges, respective particle size distributions being determined selectively for sizes in each size range using inverse modelling for the size range, positions and/or widths of successive ones of the size ranges each being selected based on the particle size distribution determined for a previous one of the size ranges, a size resolution in the size range being changed in correspondence with the selected width. In an embodiment, the widths of a next size range may be selected so that particle sizes at an edge of a previous size range are excluded for which less than a threshold density was determined in using the previous size range.

Similarly, an ultrasound measuring apparatus is provided comprising a first ultrasound transducer and a second ultrasound transducer;

a measurement cell having a first and second wall defining an interior space between the first and second wall, the first and second ultrasound transducer being located on the first and second wall respectively, with the walls and the interior space between the transducers;

a processing system configured to receive a transmission response received by the second transducer in response to ultrasound transmitted by the first ultrasound transducer and/or a reflection response received by the first transducer from the measurement cell in response to ultrasound transmitted by the first ultrasound transducer;

compute ultrasound frequency dependent ultrasound speed and/or attenuation data of ultrasound in the medium from the transmission response and/or the reflection response as a function of the ultrasound frequency, and to estimate a particle size distribution of particles in the medium by using a processing system to apply an inverse modelling algorithm to the ultrasound frequency dependent transmission response, for iteratively successive size ranges, respective particle size distributions being determined selectively for sizes in each size range using inverse modelling for the size range, positions and/or widths of successive ones of the size ranges each being selected based on the particle size distribution determined for a previous one of the size ranges, a size resolution in the size range being changed in correspondence with the selected width. In an embodiment, the widths of a next size range may be selected so that particle sizes at an edge of a previous size range are excluded for which less than a threshold density was determined in using the previous size range

The invention claimed is:

1. A method of ultrasound reflection measurement using a measurement cell containing a medium and a first ultrasound transducer and a second ultrasound transducer on mutually opposite first and second walls of the cell respectively, the method comprising transmitting ultrasound from the first ultrasound transducer to the second ultrasound transducer and from the second ultrasound transducer to the first ultrasound transducer, through the walls of the measurement cell and the medium between the walls, while the medium is present in the cell;

detecting a first and second reflection response, while the medium is present in the cell, using the first and second ultrasound transducer respectively in response to their own transmissions;

using the second and first ultrasound transducer to detect a first and second transmission response to the ultrasound, while the medium is present in the cell, transmitted by the first and second ultrasound transducer respectively;

computing an ultrasound frequency dependent ratio of a Fourier transform value of a product of signals obtained from the first and second transmission response and a Fourier transform value of a product of signals obtained from the first and second reflection response;

computing ultrasound frequency dependent ultrasound speed and/or attenuation data of ultrasound in the medium from said ratio as a function of the ultrasound frequency.

2. A method according to claim 1, wherein said transmitting comprises transmitting a first ultrasound pulse from the first ultrasound transducer to the second ultrasound transducer and transmitting a second ultrasound pulse from the second ultrasound transducer to the first ultrasound transducer, a processing system obtaining the signals obtained from the first and second reflection response by extracting earliest received pulses the first and second reflection response.

3. A method according to claim 2, wherein the processing system obtains the signals obtained from the first and second transmission response by extracting earliest received pulses the first and second transmitted response.

4. A method according to claim 1, comprising estimating a particle size distribution of particles in the medium by using a processing system to apply an inverse modelling algorithm to the ultrasound frequency dependent ultrasound speed and/or attenuation data obtained from said ratio.

5. A method according to claim 4, wherein the inverse modelling algorithm uses input data that depends on a derivative with respect to ultrasound frequency of the ultrasound speed represented by said ratio and/or on a derivative with respect to ultrasound frequency of the ultrasound attenuation represented by said ratio.

6. A method according to claim 5, wherein the inverse modelling algorithm uses a forward model that predicts the derivatives of ultrasound frequency dependent ultrasound speed and attenuation dependent on the particle size distribution and a mass density of particles in the medium, the inverse modelling algorithm being used to obtain combined estimates of the particle size distribution and the mass density from the ultrasound frequency dependent ultrasound speed and/or attenuation data obtained from said ratio.

7. A method according to claim 1, comprising growing the particles while the medium is circulated and detecting the first and second reflection response and the first and second transmission response during said growing.

8. A method according to claim 7, comprising circulating the medium during said growing through a conduit in a probe bar that extends into the vessel, the walls being part of the conduit, the conduit running from an first opening to the vessel at an end surface of said bar to a second opening to the vessel on a side surface of said bar.

9. A non-transitory computer readable medium, comprising a computer program embodied thereon, the computer program comprising instructions for a programmable processing system that, when executed by the programmable processing system, will cause the programmable processing system to use detected ultrasound reflection and transmission response to compute ultrasound frequency dependent ultrasound speed and attenuation data according to the method of claim 1.

10. An ultrasound measuring apparatus comprising a first ultrasound transducer and a second ultrasound transducer;

a measurement cell for containing a medium and having a first and second wall defining an interior space between the first and second wall, the first and second ultrasound transducer being located on the first and second wall respectively, with the walls and the interior space between the transducers;

a processing system configured to receive detected ultrasound responses from first and second ultrasound transducer, including a first and second transmission response received by the second and first transducer, while the medium is present in the cell, in response to ultrasound transmitted by the first and second ultrasound transducer respectively and a first and second reflection response received by the first and first transducer from the measurement cell, while the medium is present in the cell, in response to their own transmissions respectively; and to compute an ultrasound frequency dependent ratio of a Fourier transform value of a product of signals obtained from the first and second transmission response and a Fourier transform value of a product of signals obtained from the first and second reflection response; and to compute ultrasound frequency dependent ultrasound speed and/or attenuation data of ultrasound in the medium from said ratio as a function of the ultrasound frequency.

11. An ultrasound measuring apparatus according to claim 10, wherein the first and second wall have flat surfaces facing the interior space.

12. An ultrasound measuring apparatus according to claim 10, wherein the processing system is configured to cause the first and second ultrasound transducer to transmit ultrasound pulses, the processing system being configured to obtain the signals obtained from the first and second reflection response by extracting earliest received pulses the first and second reflection response to the transmitted pulses.

13. An ultrasound measuring apparatus according to claim 12, wherein the processing system is configured to obtain the signals obtained from the first and second transmission response by extracting earliest received pulses the first and second transmitted response.

14. An ultrasound measuring apparatus according to claim 10, wherein the processing system is configured to estimate a particle size distribution of particles in the medium by applying an inverse modelling algorithm to the ultrasound frequency dependent ultrasound speed and/or attenuation data obtained from said ratio.

15. An ultrasound measuring apparatus according to claim 14, wherein the inverse modelling algorithm uses input data that depends on a derivative with respect to ultrasound frequency of the ultrasound speed represented by said ratio and/or on a derivative with respect to ultrasound frequency of the ultrasound attenuation represented by said ratio.

16. An ultrasound measuring apparatus according to claim 15, wherein the processing system is configured to use a forward model in said inverse modelling algorithm that predicts the derivatives of the ultrasound frequency dependent ultrasound speed and attenuation dependent on the particle size distribution and a mass density of particles in the medium, the processing system is configured to use the inverse modelling algorithm to obtain combined estimates of the particle size distribution and the mass density from the ultrasound frequency dependent ultrasound speed and/or attenuation data obtained from said ratio.

17. An ultrasound measuring apparatus according to claim 10, comprising a support structure with a channel through said support structure, part of a wall of the channel being formed by the walls of the measuring cell, the channel running from a first opening on a side surface of said support structure to a second opening in an end surface of said support structure, the end surface at the second opening forming a non-zero angle with the side surface at the first opening.

18. An ultrasound measuring apparatus according to claim 17, wherein the support structure is a sensing bar, the first opening being located on a side surface the sensing bar and the second opening being located in a tip surface of the sensing bar.

* * * * *